United States Patent [19]
Graham et al.

[11] Patent Number: 5,177,694
[45] Date of Patent: Jan. 5, 1993

[54] COMPUTERIZED COLOR MATCHING

[75] Inventors: Martin A. S. Graham; Iain Cartwright, both of The Gap, Australia

[73] Assignee: Garibaldi Pty Ltd., Australia

[21] Appl. No.: 684,905

[22] PCT Filed: Jul. 14, 1989

[86] PCT No.: PCT/AU89/00297
§ 371 Date: Apr. 30, 1991
§ 102(e) Date: Apr. 30, 1991

[87] PCT Pub. No.: WO90/00733
PCT Pub. Date: Jan. 25, 1990

[30] Foreign Application Priority Data

Jul. 14, 1988 [AU] Australia ................. PI9295

[51] Int. Cl.$^5$ ............................. G01N 21/25
[52] U.S. Cl. .................. 364/526; 356/421
[58] Field of Search ............ 364/526, 502, 525; 356/402, 404, 405, 408, 421

[56] References Cited

U.S. PATENT DOCUMENTS

| | | | |
|---|---|---|---|
| 4,422,759 | 12/1983 | Holman et al. | 356/421 |
| 4,654,794 | 3/1987 | O'Brien | 364/413.28 |
| 4,813,000 | 5/1989 | Wyman et al. | 364/502 |
| 4,836,674 | 6/1989 | Lequime et al. | 356/319 |
| 4,967,379 | 10/1990 | Ott | 364/526 |

FOREIGN PATENT DOCUMENTS 261091 3/1964 Australia.
771805 4/1957 United Kingdom.

*Primary Examiner*—Parshotam S. Lall
*Assistant Examiner*—Michael Zanelli
*Attorney, Agent, or Firm*—Laurence R. Brown

[57] ABSTRACT

A method of computerized color matching for articles where articles are photographed, using a still video camera, against a set of reference colors. The photographs are stored on a diskette (34) which is read on a recorder (54). The computer (55) compares the set of reference colors against an absolute set of colors and generates a compensation factor which is applied to the photographed colors to produce a corrected photograph. Areas of the corrected photograph may be selected for computer enhancement and a computer generated map may be produced to enable the color of other articles to be matched to the photographed articles.

6 Claims, 5 Drawing Sheets

COMPUTERIZED COLOR MATCHING

BACKGROUND OF THE INVENTION (1) Field of the Invention

THIS INVENTION relates to a method of, and apparatus for, computerised colour matching.

(2) Prior Art

Colour matching is a major problem in many industries, including automobile repair; paint and dye manufacture; printing; and fabric dyeing.

Tooth colour matching is a major problem for dentists and dental technicians when preparing dental caps, crowns or bridge work. They must seek to match the cap, or teeth on the bridge, to the surrounding natural teeth. At present the method is subjective and the results very much dependent on the skills of the person doing the colour matching.

The dental technician is supplied with a "colour map" of the tooth by the prescribing dentist or the map may be drawn by the dental technician, the map being made by comparison with standard porcelain chips. From that "colour map", the technician must build the dental caps/or prosthetic teeth being aware of the following problems:

(a) the dentist and the technician are most likely to have different colour perceptions of the colours under a standard reference light, let alone under different lights;

(b) there are variations in the colour of the porcelain powders as supplied by the various manufacturers against standard "shades" (or coded colours);

(c) some of the standard shades are very similar and therefore difficult to separate by eye;

(d) the depth of the dentine layer (or its translucency) affects the final colour; and (e) the moisture content of the porcelain mix, the mix density, the firing frequency and temperature and the permeation of oxides through the opaque layer all affect the final colour.

Because of all these problems, colour mismatches may occur 10+% of the time.

In an effort to reduce the problem, a colour mixture indicator device as disclosed in U.S. Pat. No. 4,657,399 (Neil R. Hall) was developed where colour samples were provided in an array where the selected colour is either one of the samples or a mixture of the colour of two adjacent samples.

While this indicator is an improvement over the conventional porcelain colour chips, colour mismatches still occur.

SUMMARY OF THE PRESENT INVENTION

It is an object of the present invention to overcome, or at least minimize, the colour mismatches which can occur.

It is a preferred object to provide a method which can incorporate compensation factors to relate all colours against set standards.

It is a further preferred object to provide a method where the colours are measured against, colour corrected, even, constant light.

It is a still further preferred object to provide a method where the colours are measured in computer processable form, enabling a "colour corrected" map to be generated.

It is a still further preferred object to provide a suitable light source for effecting the method.

Other preferred objects of the present invention will become apparent from the following description.

In one aspect the present invention resides in a method of computerised colour matching of a first article with one or more other articles with which it is, or is to be, associated, the method including the steps of:

placing a reference set of colours adjacent the associated articles;

taking a photograph of the associated articles and the reference set of colours;

analysing the data from the photograph; and generating a colour map and/or computer enhanced photograph of the associated articles using a computer, the colour map and/or enhanced photograph identifying the colour(s) of the associated articles relative to an absolute set of colours.

Preferably the computer compares the reference set of colours against the absolute reference set of colours to determine the compensation factor required to bring the reference set of colours into conformity with the absolute reference set, and applies this compensation factor to the colours of the associated articles (as photographed) to produce a corrected picture.

A specific analysis area of the corrected picture may be computer enhanced and the resultant enhanced picture may be printed to enable comparison of the colour(s) of the associated articles as photographed with the enhanced colours of the associated articles against the absolute reference set.

A "palette" of standard shades, for the mixing of the colour of the first article, may be overlaid on the corrected photograph and a computer generated map of the shades is produced. From this map, the colour(s) of the first article may be mixed.

In a dental application, a porcelain key overlay is overlaid as the colour palette to show the different shades to be mixed and their relative locations in the cap or prosthetic tooth.

In a second aspect the present invention resides in apparatus for effecting the computerised colour matching of the first article against the associated articles, the apparatus including:

means to support a reference set of colours adjacent the associated articles;

reference light means to illuminate the associated articles and the reference set of colours;

still video camera means to photograph the associated articles and the reference set of colours in machine readable form;

computer means to analyse the reference set of colours against an absolute set of colours, to calculate a compensation factor to compensate for the difference between the reference set and absolute set of colours and to produce a corrected picture where the colours of the associated articles have been corrected by the compensation factor; and output means to generate a colour map and/or enhanced photograph identifying the colour(s) of the associated articles relative to the absolute set of colours.

In a third aspect the present invention resides in a light unit for the illumination of articles to be photographed including:

a housing;

a light diffusing chamber extending through the housing, one end of the diffusing chamber having a mouth arranged to be positioned against, or adjacent, the article and the other end of the diffusing chamber being arranged to receive a lens assembly (or body) of a camera;

a light tunnel enclosing at least a portion of the length of the diffusing chamber, an opaque wall separating the light tunnel from the diffusing chamber at the other end of the diffusing chamber; and a light box, containing at least one light source, connected to the light tunnel so arranged that light from the light sources travels through the light tunnel and into the diffusing chamber to illuminate the article to be photographed.

Preferably diffuser means are provided between the light tunnel and the diffusing chamber to diffuse the light entering the diffusing chamber.

One or more colour correction filters may be provided in the light tunnel.

One or more prisms may be provided at the end(s) of the light tunnel to create a "flat even light field" effect onto the articles.

For dental applications, a removable, flexible mouth piece may be provided to engage the teeth, and retract the lips, of the person whose teeth are to be photographed.

Preferably the mouth piece, on the mouth of the diffusing chamber, includes means to releasably support a plate means having a reference set of colours thereon.

Preferably the other end of the diffusing chamber is releasably engageable, e.g. by a bayonet fitting, to the lens system (or body) of the camera.

BRIEF DESCRIPTION OF THE DRAWINGS

To enable the invention to be fully understood, a preferred embodiment will now be described with reference to the accompanying drawings, in which.

DETAILED DESCRIPTION OF THE PREFERRED EMBODIMENT

The invention will be described with reference to the colour matching of dental caps or prosthetic teeth.

Figure 1:
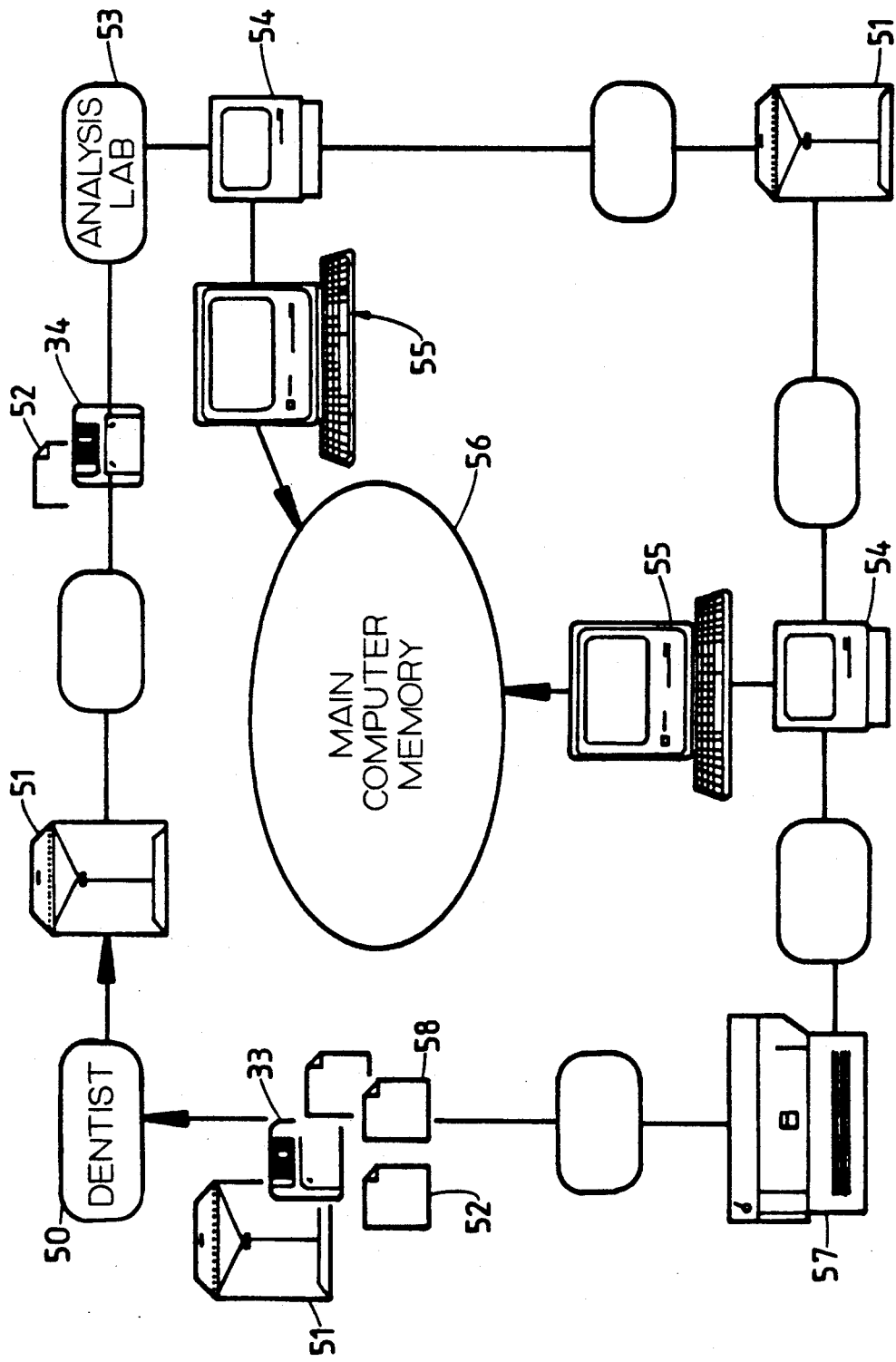
FIG. 1 is a flow diagram of a system for the colour matching of dental caps or prosthetic teeth using the present invention.

FIG. 1 is a flow chart of the hardware and software employed in the method.

Using the light unit 10 (see FIGS. 2 and 3) and the still video camera 11 (see FIG. 4), the dentist takes two photographs of the patient's teeth. The first photograph is a general photograph of the teeth to give the dental technician details of the shape and spacing of the teeth (and the general colour variation in the teeth throughout the mouth). The second photograph is taken with the standard reference strip 12 (which may comprise samples of the 16 reference porcelain shades) to enable the actual colours (and shade variations) of the teeth to be matched.

Figure 2:
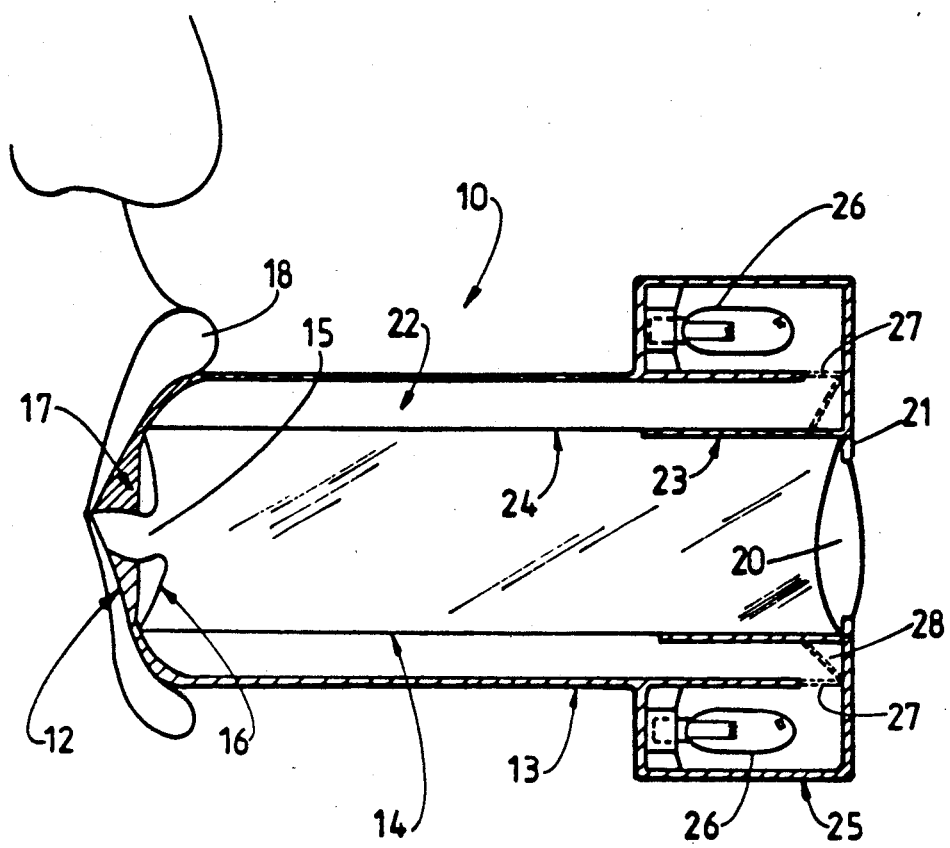
FIG. 2 is a sectional side view of the light unit.
Figure 3:
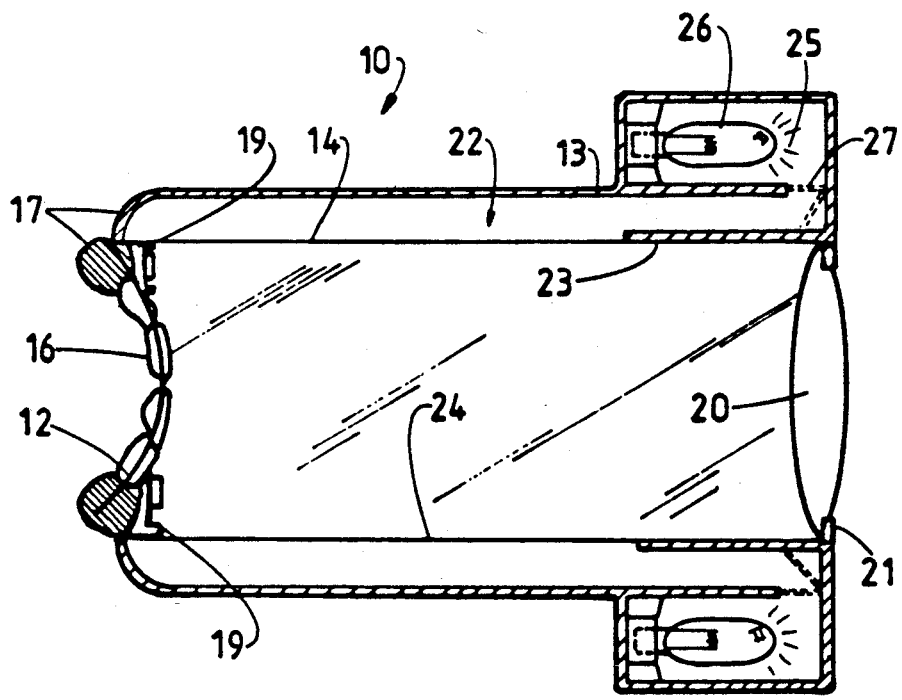
FIG. 3 is a sectional top plan view of the light unit in use.
Figure 4:
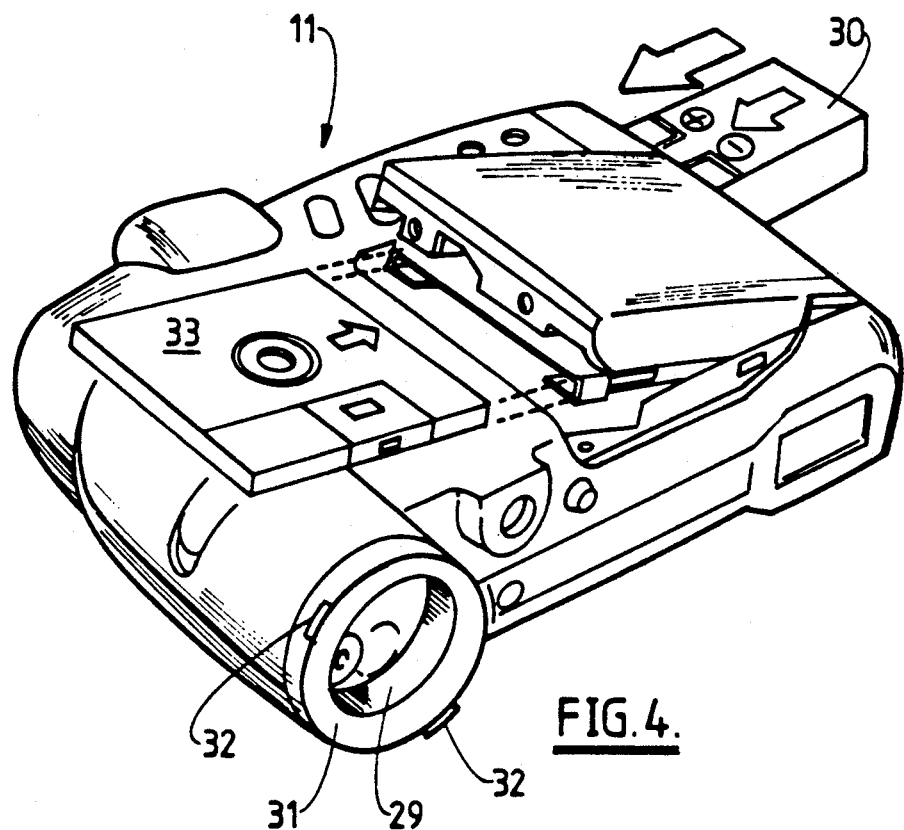
FIG. 4 is a perspective view of a still video camera suitable for use with the light unit.
Figure 5:
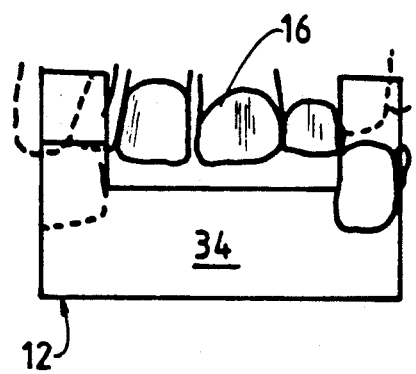
FIG. 5 is a front view of the standard reference colour strip in front of a person's teeth.
Figure 6:
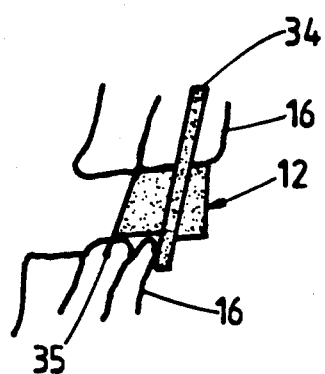
FIG. 6 is a side view corresponding to FIG. 5.

Referring to FIGS. 2 and 3, the light unit 10 has a housing 13 (e.g. of injection moulded plastics material). A light diffusing chamber 14 extends coaxially through the housing 13 and at one end is provided with a mouth 15 adapted to be positioned adjacent to the patient's teeth 16. The housing 13 is provided with a removable, flexible plastic mouth piece 17 which is curved in top plan view, to bear against the front of the patient's teeth and to retract the patient's lip 18.

Locating pins 19 in the mouth 15 locate the standard reference strip 12 in front of the teeth (see FIG. 3).

An optical lens 20 is mounted at the other end of the diffusing chamber 14 just inwardly off the female portion of a bayonet coupling 21 which enables the light unit 10 and camera 11 to be releasably connected together. A light tunnel 22 surrounds the diffusing chamber 14 and is separated therefrom by a solid wall 23 adjacent the lens 20 and a light diffusion assembly 24.

A light box 25 surrounds the end of the light tunnel 22 spaced from the mouth piece 17 and this contains one or more incandescent globes 26. The light from the globes 26 passes through a colour correction filter 27 into the light from tunnel 22, the solid wall 23 preventing the light entering the diffusing chamber directly. The lights in the light tunnel 22 fully surround the diffusing chamber 14.

Figure 9:
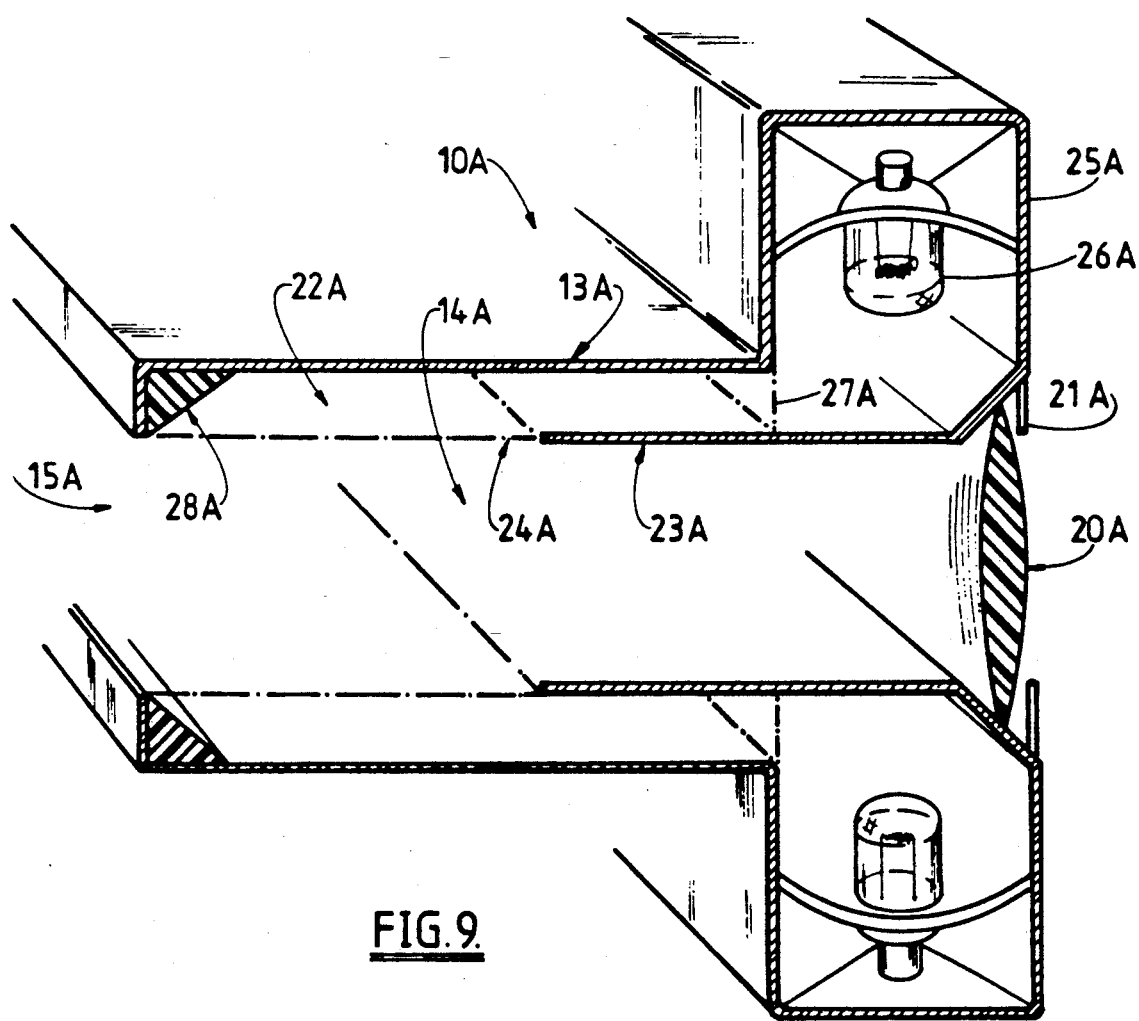
FIG. 9 is a sectional side view of a second embodiment of the light unit.

As shown in FIGS. 2 and 9, optical prisms 28 may be provided at the ends of the light tunnel 22 to assist the diffusion of the light through the unit and create a "dome light" effect which removes any shadows on the patient's teeth 16.

The camera 11 is a "Canon RC-250" still video camera produced by Canon Inc., Tokyo, Japan which has minor modifications made to it. The optional "macro" lens 29 is substituted for the standard lens and the light unit 10 is electrically connected to, and powered by, the camera's battery 30 and electronics. The male portion of the bayonet coupling 31 has pins 32 engageable with the light unit 10 to releasably secure the light unit 10 and camera 11 together with the optical lens 20 and the camera's "macro" lens 29 closely adjacent. The photographs taken by the camera 11 are stored on a removable diskette 33.

The colour reference strip 12 (see FIGS. 5 to 8) has a generally planar plastic body 34 which is U-shaped in front view and samples 35 of different porcelain shades are provided on the front face thereof.

Figure 7:
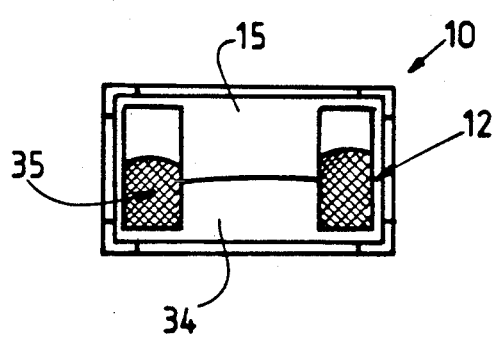
FIG. 7 is a front view of the reference strip fitted to the light unit.
Figure 8:
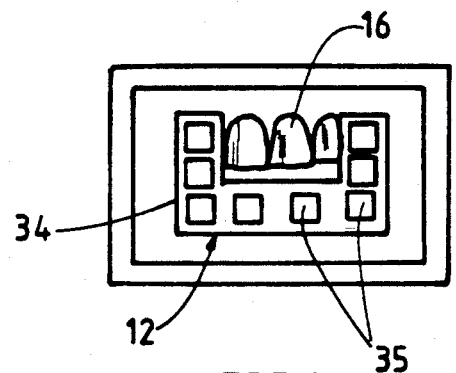
FIG. 8 is a view of the teeth and reference strip as seen by the camera.

Blocks 36 are provided on the rear of the body 34 to enable the strip 12 to be gripped by the patient's teeth 16. As shown in FIGS. 7 and 8, the strip 12 is fitted in the mouth 15 of the light unit 10. As shown in FIG. 8, the strip 12 forms a "window" 34 about the teeth 16 being photographed.

FIG. 9 shows a modified form of the light unit 10A where features common to the light unit 10 are indicated by the letter "A" (i.e. lens 20A corresponds to the lens 20 of the light unit 10).

The method will now be described referring back to FIG. 1.

Each diskette is permanently marked with an identifying number (ID) externally and the ID is carried on the first five tracks in machine readable form. The photograph of the patient's teeth and gums, and of the same field with the reference strip 12 (see FIG. 8) are recorded on the next two tracks.

The dentist 50 places the diskette 34 in a courier satchel 51, accompanied by a duplicate service request form 52. The satchel 51 is permanently marked with the name and address of the dentist and with an ID number unique to the camera 11 used by the dentist. The request form 52 contains the patient's identification and the ID number of the diskette.

The satchel is transported to the analysis laboratory 53 by the courier. The operator places the diskette 34 in a still video disc player 54 and enters the patient's identification, camera ID and diskette ID into the computer 55.

From the data read by the player 54 from the diskette 34, the operator selects the areas of the pictures and the tooth colours to be analysed. The analysis of the photographs produces a packet of data that contains:
(a) the patient's information;
(b) the camera and diskette ID numbers;
(c) the track numbers of the photographs; and
(d) the "porcelain key" overlay.

This packet of data is stored temporarily in the main computer memory 56, indexed by the diskette ID number.

After the diskette 34 has been read in the player 54, it is placed in the satchel 51 and is retrieved and placed in the disc player 54' and enters the camera ID number from the satchel 51.

The operator confirms the correct overlay of patient data on the proper diskette track.

The computer compares the colour reference strip 12 as photographed with an absolute reference strip and generates a compensation factor to bring the two into conformity. This correction factor is applied to the photograph data to create a corrected photograph which is printed on a printer 57.

The corrected photograph has the analysis area, previously selected by the operator, enhanced and the "enhanced photograph" is then printed.

Figure 10:
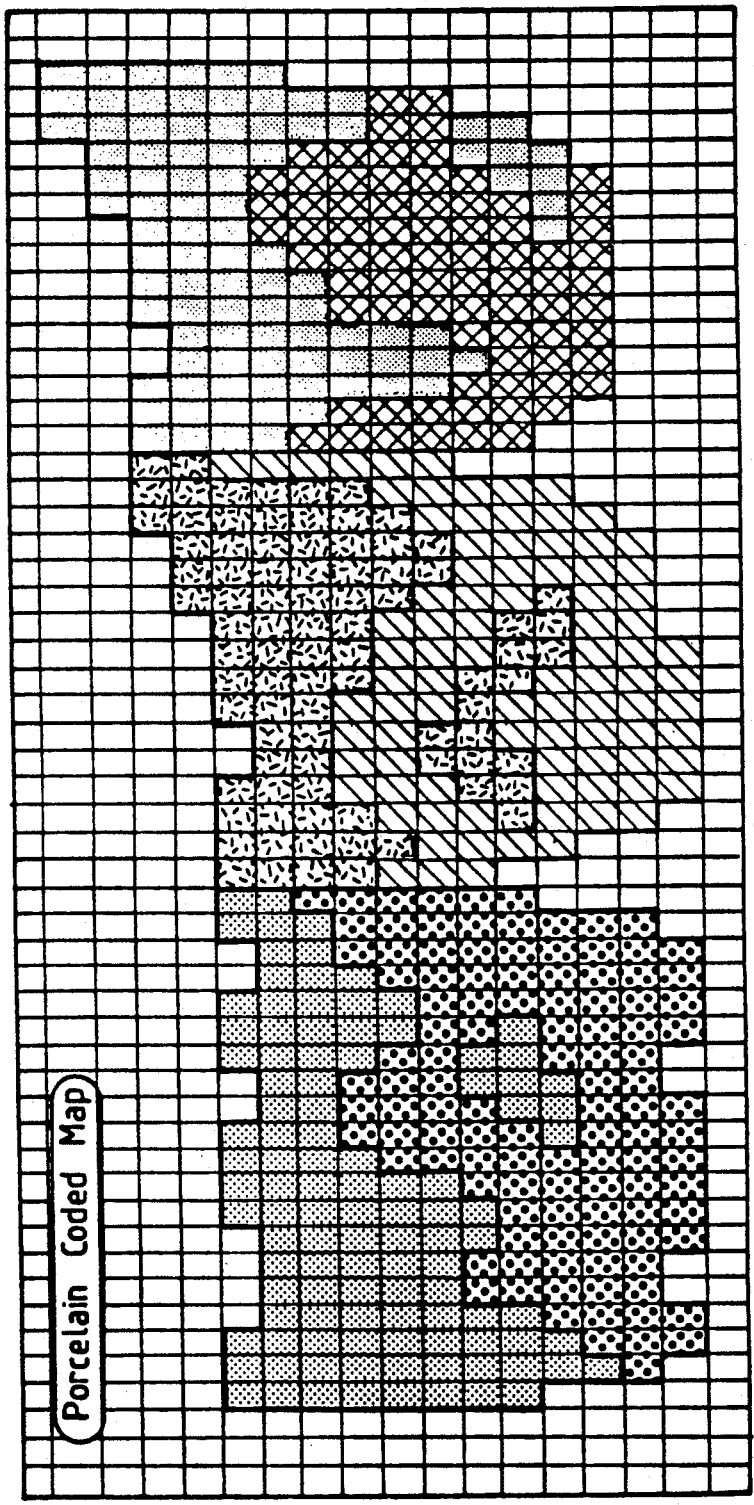
FIG. 10 is an example of the porcelain coded map produced by the method of the present invention.

The "porcelain key overlay", which shows the different shades of porcelain, is overlaid over the enhanced photograph and the porcelain coded map (FIG. 10) is generated. The corrected picture is overlaid with a machine readable code and this picture and the computation code overlaid thereon is recorded back into the diskette 34.

An invoice 58 is printed and this is placed in the satchel, together with the diskette and the original service request form and returned to the dentist 50 by courier.

From the porcelain coded map supplied by the dentist, the dental technician can proceed to produce the dental cap or prosthetic tooth using his professional skills. As he knows that the coded map has been produced relative to a fixed set of standards, he can accurately match the colour of the cap or prosthetic tooth to the patient's teeth using his professional skills and his knowledge of the porcelain powder components and preparation conditions.

As an example, the porcelain coded map may instruct the technician to produce a prosthetic tooth, which may incorporate a high platinum/gold ratio pin, or fitted over a ground-down tooth, with an A1 shade root, A2 shade denture and A3 shade enamel to match the surrounding teeth 16 in the patient's mouth.

In addition, by being presented with the two original photographs taken by the dentist (in printed form), the enhanced photograph produced by the computer (in printed form), he has full details of the patient's mouth including shape of the adjacent teeth and any blemishes, changes of colour therein and any underbite/overbite between the patient's jaw. All of this information results in a much higher quality, more accurate product.

It will be readily apparent to the skilled addressee that this method is applicable to many other area where colour matching is required e.g. matching paints or dyes, prosthetic eyes, as hereinbefore described.

For example, the data generated by the computer can be in the form of base paint or dye/tint ratios so that the colour of the first article, when painted or dyed in accordance with the ratios, will match the colours of the associated articles.

Various changes and modifications may be made to the example described without departing from the scope of the present invention defined in the appended claims.

We claim:

1. A method of computerized colour matching of a first article with one or more other articles which the first article may be, associated, the method including the steps of:
   placing a strip displaying a reference set of colours adjacent the associated articles;
   taking a photograph of the associated articles and the reference set of colours;
   analyzing the colour data from the photograph; and
   generating a colour map and/or computer enhanced photograph, of the associated articles, using a computer, the colour map and/or enhanced photograph identifying the colour(s) of the associated articles relative to an absolute set of colours.

2. A method as claimed in claim 1 wherein:
   the computer compares the reference set of colours against the absolute reference set of colours to determine the compensation factor required to bring the reference set of colours into conformity with the absolute reference set, and applies this compensation factor to the colours of the associated articles (as photographed) to produce a corrected picture.

3. A method as claimed in claim 2 wherein:
   a specific analysis area of the corrected picture is computer enhanced and the resultant enhanced picture is printed to enable comparison of the colour(s) of the associated articles as photographed with the enhanced colours of the associated articles against the absolute reference set.

4. A method according to claim 3 wherein:
   a "palette" of standard shades, for the mixing of the colour of the first article, is overlaid on the corrected photograph and a computer generated map of the shades is produced.

5. An apparatus for effecting the computerized colour matching of a first article against one or more articles with which the first article may be associated, the apparatus including:
   means to support a strip displaying a reference set of colours adjacent the associated articles;
   reference light means to illuminate the associated articles and the reference set of colours;
   still video camera means to photograph the associated articles and the reference set of colours in machine readable form;
   computer means to analyze the reference set of colours against an absolute set of colours, to calculate a compensation factor to compensate for the difference between the reference set and absolute set of colours and to produce a corrected picture where the colours of the associated articles have been corrected by the compensation factor; and output means to generate a colour map and/or enhanced photograph identifying the colour(s) of the associated articles relative to the absolute set of colours.

6. A method of computerized colour matching of a first article with one or more other articles with which the first article may be associated, the method including the steps of:

placing a strip displaying a reference set of colours adjacent the associated articles;

taking a photograph of the associated articles and the reference set of colours;

analyzing the colour data from the photograph; and generating base paint or dye/tint mixing ratios to enable the colour of the first article, when painted or dyed in accordance with the ratios, to match the colour of the associated articles.

* * * * *